(12) United States Patent
van der Meijden et al.

(10) Patent No.: US 12,729,365 B2
(45) Date of Patent: Sep. 8, 2026

(54) BIOMASS REACTOR AND PROCESS

(71) Applicant: Nederlandse Organisatie voor toegepast-natuurwetenschappelijk Onderzoek TNO, 's-Gravenhage (NL)

(72) Inventors: Christiaan Martinus van der Meijden, 's-Gravenhage (NL); Hendrica Johanna Maria Visser, 's-Gravenhage (NL)

(73) Assignee: Nederlands Organisatie voor toegepast—natuurwetenschappeljikOnderzoek TWO, 's-Gravebhage (NL)

( * ) Notice: Subject to any disclaimer, the term of this patent is extended or adjusted under 35 U.S.C. 154(b) by 592 days.

(21) Appl. No.: 18/252,195

(22) PCT Filed: Nov. 9, 2021

(86) PCT No.: PCT/EP2021/081094
§ 371 (c)(1),
(2) Date: May 9, 2023

(87) PCT Pub. No.: WO2022/101190
PCT Pub. Date: May 19, 2022

(65) Prior Publication Data

US 2023/0407233 A1 Dec. 21, 2023

(30) Foreign Application Priority Data

Nov. 10, 2020 (EP) .................................... 20206613

(51) Int. Cl.
*C12M 1/00* (2006.01)
*C10B 7/00* (2006.01)
*C12M 1/02* (2006.01)

(52) U.S. Cl.
CPC ............ *C12M 45/20* (2013.01); *C12M 41/20* (2013.01)

(58) Field of Classification Search
CPC ......... C12M 41/20; Y02E 50/10; C10B 49/04
See application file for complete search history.

(56) References Cited

U.S. PATENT DOCUMENTS 2,380,930 A 8/1945 Andersen et al.
4,276,120 A 6/1981 Lutz
(Continued)

FOREIGN PATENT DOCUMENTS

AU 465 554 B2 10/1975
AU 2021106888 A4 * 11/2021 ............. C10L 5/447
(Continued)

*Primary Examiner* — Nathan A Bowers
(74) *Attorney, Agent, or Firm* — Ipsilon USA—NLO

(57) ABSTRACT

Reactor for processing biomass, e.g. into biochar or bio cokes, with a reactor enclosure (2) having a transport unit (5). In a first reactor section (6) first gas injectors (11) are positioned below the transport unit (5), and first oxidant injectors (12) are positioned above transport unit (5). In a second reactor section (7) second gas injectors (13) are positioned below the transport unit (5), and second oxidant injectors (14) are positioned above the transport unit (5). In a the third reactor section (8) third gas injectors (15) are provided below the transport unit (5). The first, second and third gas injectors (11, 13, 15) are further arranged to output a first, second, and third gas, respectively, each having a low oxygen content, and the first and second oxidant injectors (12, 14) are arranged to output an oxidizing gas only for providing radiation heat energy, using a control unit (20).

17 Claims, 2 Drawing Sheets

(56) References Cited

U.S. PATENT DOCUMENTS

Figure 1A:
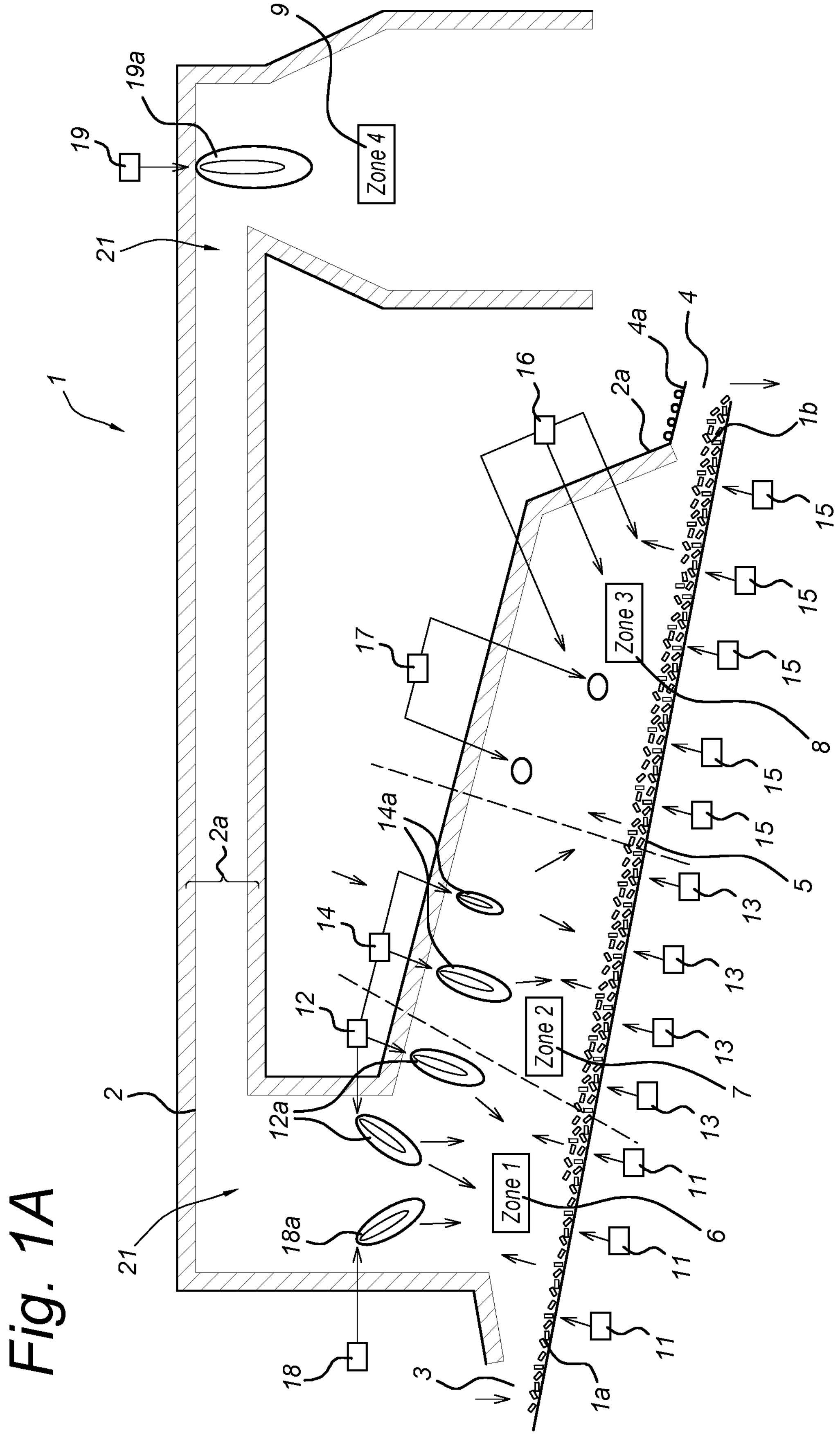

| | | | | |
|---|---|---|---|---|
| 6,270,554 | B1 * | 8/2001 | Queneau | C22B 23/025 75/677 |
| 8,685,121 | B2 * | 4/2014 | Surma | C03B 5/025 48/197 R |
| 2005/0204969 | A1 * | 9/2005 | Capote | F23G 5/444 110/341 |
| 2011/0136971 | A1 * | 6/2011 | Tucker | C10G 1/002 977/788 |
| 2012/0193581 | A1 * | 8/2012 | Goetsch | F23G 5/30 252/373 |
| 2013/0142723 | A1 * | 6/2013 | Dara | C10J 3/723 422/106 |
| 2014/0311883 | A1 * | 10/2014 | Strezov | C10B 7/00 201/20 |
| 2020/0325399 | A1 * | 10/2020 | Gai | C10J 3/84 |

FOREIGN PATENT DOCUMENTS

| | | | | | |
|---|---|---|---|---|---|
| CA | 2680135 | A1 | * | 11/2008 | C10J 3/723 |
| CA | 2864089 | A1 | * | 8/2013 | C10B 53/07 |
| JP | 2003166705 | A | * | 6/2003 | |
| WO | 2020/212198 | A1 | | 10/2020 | |

* cited by examiner

Zone 1
Zone 2
Zone 3
Zone 4
1
1a
1b
2
2a
3
4
4a
5
6
7
8
9
11
12
12a
13
14
14a
15
16
17
18
18a
19
19a
21

BIOMASS REACTOR AND PROCESS

FIELD OF THE INVENTION

The present invention relates to a reactor for processing biomass, comprising a reactor enclosure having an input for receiving biomass and an output for outputting processed biomass, and a transport unit for transporting biomass in the reactor enclosure from the input to the output. The biomass is e.g. transformed into biochar, bio cokes, and the like, using gasification and/or pyrolysis as main process.

BACKGROUND ART

International patent publication WO2014/155058 discloses a method and apparatus for producing biochar. The biochar is produced from woody biomass, and the method disclosed includes the steps of (a) placing feedstock in a first kiln; (b) burning fuel in an oxidiser and directing the resultant heated gases from the oxidiser to the feedstock to reduce the moisture content of the feedstock; (c) burning fuel in an oxidiser and directing the resultant heated gases from the oxidiser to the feedstock to subject the feedstock to pyrolysis; (d) removing at least some of the pyrolytic gases, released from the feedstock in step c, to the oxidiser for burning therein; (e) directing at least a portion of the at least partially inert gases resultant from the burning of the pyrolytic gases in step d to the feedstock to regulate the amount of heat and air supplied to the kiln to controllably continue pyrolysis of the feedstock therein.

International patent publication WO2017/204703 discloses a process and reactor for producing biochar from renewable material. A biomass material is supplied into a material chamber of the reactor, and the biomass material is dried by evaporating moisture from the biomass material. The biomass material is then subjected to pyrolysis to obtain biochar and pyrolysis gas. Gasification air and pyrolysis gas is supplied to a reaction chamber in the reactor, and gasification air and pyrolysis gas are combusted in the reaction chamber. Exhaust gas is removed from the reaction chamber. The biomass material is heated by indirect heat from the exhaust gas.

Australian patent publication AU-B-465 554 discloses an apparatus for the carbonization of coal, comprising a travelling bed, a carbonization chamber, hot gas inlets in the carbonization chamber below the travelling bed, and air inlets (oxidants) in the combustion chamber to support combustion of coal volatiles carried by hot gases.

US patent publication U.S. Pat. No. 4,276,120 discloses a reactor for purification of petroleum coke to produce an economical low sulfur product suitable for electrode production.

SUMMARY OF THE INVENTION

The present invention seeks to provide an efficient and cost effective production of processed biomass, such as biochar or bio cokes from biomass, with a sufficiently high yield.

According to the present invention, a reactor as defined above is provided, which further includes a first reactor section, a second reactor section positioned downstream from the first reactor section, and a third reactor section positioned downstream from the second reactor section. The first reactor section comprises first gas injectors which are positioned below the transport unit and which are arranged to output a first gas through the biomass on the transport unit during operation, and first oxidant injectors which are positioned above the transport unit and which are arranged to provide first heat sources directing radiation heat energy to the biomass during operation. The second reactor section comprising second gas injectors which are positioned below the transport unit and arranged to output a second gas through the biomass fuel on the transport unit during operation, and second oxidant injectors which are positioned above the transport unit and which are arranged to provide second heat sources directing radiation heat energy to the biomass during operation. The third reactor section comprising third gas injectors which are positioned below the transport unit and arranged to output a third gas through the biomass on the transport unit during operation. The first, second and third gas injectors are further arranged to output a first, second, and third gas, respectively, each having a low oxygen content, and the first and second oxidant injectors are arranged to output an oxidizing gas only. The reactor further comprises a control unit connected to the first, second and third gas injectors and the first and second oxidant injectors, wherein the control unit is arranged to control the amount and composition of gas mixture supplied by each of the first, second and third gas injectors and the first and second oxidant injectors. The result is a reactor allowing efficient and reliable processing of biomass with controllable radiation heat sources from above. Volatiles escaping from the biomass in the first and second reactor section are used as an energy source for the radiation heat, and subsequent further transformation of biomass material, i.e. from input to output the biomass is subjected to drying, pyrolysis and/or gasification, cooling into processed biomass, such as biochar which has high quality (free from tar, etc.).

The continuous process having these combination of features as applied in the present invention embodiments provides a more efficient way of obtaining processed biomass such as biochar, bio cokes, etc., as compared to prior art batch processing methods.

In the first reactor section, conditions can be created to start up a pyrolysis of the biomass, e.g. by the first gas injectors being arranged to output the first gas having a predefined composition (e.g. air, flue gas or a low oxygen content gas mixture) with an equivalence ratio ER of less than 0.1, e.g. 0.08), which will cause heat production by controlled flow of the low oxygen content first gas, which can react with pyrolysis gases from the biomass, in addition to drying and pyrolysis start-up of the biomass. In the second reactor section, conditions can be created to maintain a pyrolysis process of the biomass, e.g. by the second gas injectors being arranged to output a second gas with a low oxygen content, such as flue gas or an inert gas. In the second reactor section mainly stirring of the biomass on the transport unit occurs because of the tumbling action of the biomass particles caused by movement of the transport unit, and pyrolysis/gasification of the biomass is maintained using the radiation heat energy from above. Note that the first and second oxidant injectors are arranged to output an oxidizing gas only (e.g. in the form of oxygen rich air), no fuel in gas form is needed to be applied as this is provided by the gas products (volatiles) originating from the pyrolysis process below the first and second oxidant injectors.

SHORT DESCRIPTION OF DRAWINGS

Figure 1B:
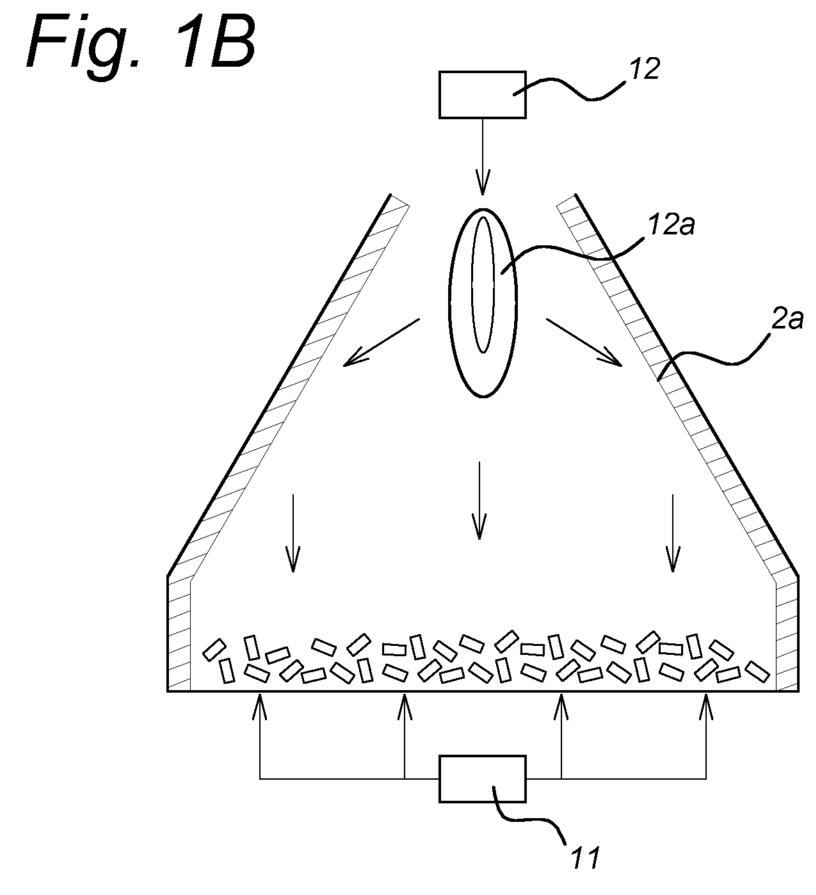

The present invention will be discussed in more detail below, with reference to the attached drawings, in which FIG. 1A shows a schematic illustration of a reactor for processing biomass according to an embodiment of the present invention in a length wise cross sectional view, and FIG. 1B shows a cross sectional view perpendicular to the FIG. 1A view.

Figure 2:
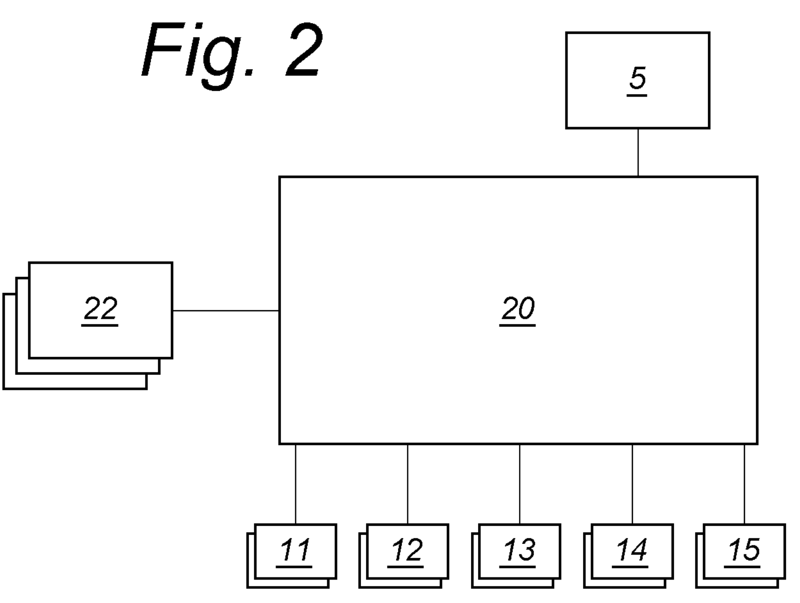

FIG. 2 shows a schematic diagram of a control arrangement for a reactor for processing biomass production according to an embodiment of the present invention.

DESCRIPTION OF EMBODIMENTS

Biomass can be processed into many different (semi-) products, such as biochar or bio cokes. Biochar is a charcoal-like substitute that is primarily produced for agricultural purposes. It is commonly used as a soil amendment to improve soil quality and enhance soil fertility, or as peat replacement in potting soil. It has also been shown that biochar increases soil carbon sequestration, reducing the carbon footprint of agricultural practices. Bio cokes can be used as a replacement for charcoal in steel production, making it a more sustainable process.

Similar to charcoal, biochar and bio cokes are produced by heating biomass at elevated temperatures in an oxygen-deficient environment. The biomass undergoes several stages during this thermal process, where the volatile content matter of the biomass is released in a gaseous form, and the remaining substance at the end is collected as biochar. This thermal process is more commonly known as pyrolysis or gasification (in case of an added gas stream).

There are several techniques known in the art that are able to mass produce processed biomass (biochar, bio cokes) using pyrolysis. One common technique known in the art is to use a rotary drum, also known as a rotary kiln, where biochar is produced within a rotating drum reactor. In this technique, one approach is to indirectly heat the biomass by radiation through the reactor walls. The wall temperatures are significant lower than the flame temperature in the present invention embodiments, therefor the radiation heat intensity in prior art reactors is much lower than in the present invention embodiments. The disadvantage of this approach is that this results in a largely expensive reactor, as heat transfer and rotation of the heavy drum are limited, leading to inefficient biochar production. An alternative approach is to directly heat the biomass with an internal flame within the drum reactor. However, this may lead to an environment with poor temperature control, and the risk of biomass combustion is increased due to the increased contact of the biomass with the oxygen-rich air and/or internal flame. One further disadvantage of direct heating is that the biochar yield is lower. Furthermore, one disadvantage of indirect approaches is that the heat is generated through the burning of fossil fuels or burning of cleaned gas. Fossil fuel is ideally avoided to reduce the carbon footprint of the biochar production. Using own gas requires extensive cleaning.

The present invention embodiments provide an improved reactor for producing biochar using pyrolysis and/or gasification, and a production system that overcomes the above disadvantages, offering a more heat-efficient and cost-effective process.

FIG. 1A shows a schematic illustration of a reactor for processing biomass into e.g. biochar according to an embodiment of the present invention. The reactor 1 comprises a reactor enclosure 2 having an input 3 for receiving biomass 1*a* and an output 4 for outputting processed biomass 1*b*. The biomass normally has been pre-dried prior to entering the input 3 of the reactor enclosure 2. The biomass may, for example, enter the input 3 at a rate of 10 tonnes per hour. The reactor further comprises a transport unit 5, arranged for transporting biomass in the reactor enclosure 2 from the input 3 to the output 4.

In the embodiment shown in FIG. 1, the reactor comprises three sections, a first reactor section 6, a second reactor section 7 positioned downstream from the first reactor section 6, and a third reactor section 8 positioned downstream from the second reactor section. Each reactor section plays a substantial role in the biochar, and these are explained below As shown in the embodiment of FIGS. 1A and B, the first reactor section 6 comprises first gas injectors 11 which are positioned below the transport unit 5, and which are arranged to output a first gas through the biomass 1*a*; 1*b* on the transport unit 5 during operation. The first reactor section 6 is primarily responsible for the further drying and initial pyrolysis of the biomass 1*a*; 1*b*, where this is labelled 'Zone 1' in the embodiment of FIG. 1. The biomass 1*a* enters into the first reactor section 6 from the input 3.

In a further embodiment, the first gas is air having a predefined composition with an equivalence ratio (ER) of less than 0.1, e.g. 0.08, to ensure drying and pyrolysis in the first reactor section 6. As an alternative, the first gas may be a flue gas, or a low oxygen content gas mixture.

As shown in the embodiment of FIGS. 1A and B, the first reactor section 6 further comprises first oxidant injectors 12, which are positioned above the transport unit 5, and which are arranged to provide first heat sources 12*a* directing radiation heat energy to the biomass 1*a*; 1*b* during operation. Oxidant gas injection is applied by the first oxidant injectors 12, where it forms a combustion reaction with the released pyrolysis gases (volatiles and further pyrolysis products) from the biomass on the transport unit 5. Heat radiation is produced by the first heat sources 12*a*, heating the biomass from the top, while part of the biomass is directly heated by the first gas from below the transport unit 5.

The first oxidant injectors 12 are positioned at multiple positions above the transport unit 5 in the first reactor section 6, i.e. well above the biomass 1*a*; 1*b* on the transport unit 5 during operation. By applying more oxidant air, for example, at the end of the first reactor section 6 than at the start of the first reactor section 6, a (controlled) temperature gradient may be produced in the first reactor section 6, further enhancing the initial processing steps of drying and pyrolysis start-up. The first heat injectors 12 are positioned at a distance from the transport unit 5 of at least 0.7 m, for example, at least 1 m, or even 2-3 m. This allows sufficient distance from the first heat sources 12*a* to the biomass 1*a*; 1*b* on the transport unit 5, and direct combustion of the biomass on the transport unit 5 is thus avoided.

This is shown in the cross sectional view of the reactor enclosure 2 embodiment of FIG. 1B, which also shows that in even further embodiments, the first gas injectors 11 are spread over the width of the transport unit 5 (which is e.g. 4 m wide) to enable proper first gas injection. The reactor enclosure 2 is provided with heat resistant walls 2*a*, and tapers from the transport unit 5 towards the first oxidant injectors 12, allowing to efficiently provide the first heat source 12*a*.

In the embodiment shown in FIG. 1A, pyrolysis gas is released from initial pyrolysis of the biomass 1*a*; 1*b* in the first reactor section 6 on the transport unit 5. Gas injection with low oxygen content is applied by the first gas injectors 11, where it forms combustion reactions with the released pyrolysis gas in the first reactor section. Heat energy is produced from the combustion reactions, but the biomass

1*a*; 1*b* on the transport unit 5 is predominantly heated by the heat radiation from above, thereby heat radiation is provided for the initial pyrolysis. In other words, initial pyrolysis of the biomass 1*a*; 1*b* takes place in a first reactor section 6 on the transport unit 5, forming pyrolysis gas by applying injection of a first gas with a low oxygen content through the biomass 1*a*; 1*b*, and applying oxidant injection for reaction with the formed pyrolysis gas above the biomass 1*a*; 1*b* on the transport unit 5, thereby providing radiation of heat energy onto the biomass 1*a*; 1*b*. Further pyrolysis gas is released from the biomass 1*a*; 1*b* on the transport unit 5, where further combustion reactions with the first gas injection with low oxygen content applied by the first oxidant injectors 11 are formed to further directly heat the biomass fuel on the moving bed 5. Movement of the transport unit 5 provides agitation of the biomass 1*a*; 1*b*.

The process of forming combustion reactions between the released pyrolysis gas and low oxygen content air (first gas) is the principle of producing heat for biomass pyrolysis in the present invention embodiments, in combination with using the released pyrolysis gas as a fuel for heating the biomass 1*a*; 1*b* from above by radiation. Combustion reactions on the biomass fuel on the transport unit 5 are minimized in this configuration process, as pyrolysis gas is only released from the biomass 1*a*; 1*b* on the transport unit 5, and the oxygen content of the gas injection applied by the first gas injectors 11 is low.

In the embodiment shown in FIG. 1A, the second reactor section 7 comprises second gas injectors 13 which are positioned below the transport unit 5, and which are arranged to output a second gas through the biomass 1*a*; 1*b* on the moving bed 5. The second reactor section 7 is primarily responsible for the main pyrolysis of the biomass 1*a*; 1*b* and formation of biochar/bio cokes, where this is labelled 'Zone 2' in the embodiment of FIG. 1A. The biomass fuel enters the second reactor section 7 from the first reactor section 6.

The second reactor section 7 further comprises second oxidant injectors 14, which are positioned above the transport unit 5, and are arranged to provide second heat sources 14*a* directing radiation heat energy to the biomass (1*a*; 1*b*) during operation. Similar to that in the first reactor section 6, the oxidant injection applied by the second oxidant injectors 14 forms combustion reactions with the released pyrolysis gas, and the heat radiation produced from the combustion reactions provides the second heat source 14*a* to heat the biomass 1*a*; 1*b* on the transport unit 5. The second oxidant injectors 14 are positioned at multiple positions above the transport unit 5 in second reactor section 7, where a temperature gradient in the second reactor section may also be produced. The second heat injectors 14 are positioned at a distance from the transport unit 5 of at least 0.7 m, for example, at least 1 m, or even 2-3 m, which allows sufficient distance from the second heat sources 14*a* to the biomass 1*a*; 1*b* on the transport unit 5, and direct combustion of the biomass 1*a*; 1*b* on the transport unit 5 in the second reactor section 7 is avoided.

In a further embodiment, the second gas is a gas with a low oxygen content, e.g. flue gas or an inert gas (e.g. nitrogen gas may be used). Movement of the transport unit 5 provides agitation of the biomass 1*a*; 1*b* on the transport unit 5, as to further expose all surfaces of the biomass 1*a*; 1*b* to the main pyrolysis process. The low oxygen content second gas injection applied by the second gas injectors 13 is (almost) inert such that it does not form a combustion reaction with the biomass 1*a*; 1*b* on the transport unit 5. Furthermore, the low oxygen content second gas injection applied by the second gas injectors minimizes the reaction with the released pyrolysis gas from the biofuel mass on the transport unit 5. The injected second gas also ensures that any possible tar components originating from the biomass 1*a*; 1*b* are not deposited back on the biomass 1*a*; 1*b*.

Similar to the configuration process in the first reactor section 6, the pyrolysis gas released from the biomass fuel on the transport unit 5 is the fuel for pyrolysis in the second reactor section 7. Heat radiation is produced from the combustion reactions between the pyrolysis gas released from the biomass 1*a*; 1*b* on the transport unit 5 and the oxidizing gas in the second reactor section 7, providing heat radiation for the main pyrolysis of the biomass 1*a*; 1*b* on the transport unit 5 in the second reactor section 7. Formation of processed biomass 1*a*; 1*b* takes place in the second reactor section 7 on the transport unit 5 downstream from the first reactor section 6, by pyrolysis of the biomass 1*a*; 1*b* obtained by applying injection of a second gas through the biomass 1*a*; 1*b* on the transport unit 5 and combustion of the formed pyrolysis gas above the transport unit 5, thereby providing additional radiation of heat energy onto the biomass 1*a*; 1*b*. A combustion reaction of the biomass 1*a*; 1*b* on the transport unit 5 in the second reactor section 7 is avoided by the constant application of second gas from the second gas injectors 13. Movement of the transport unit 5 provides agitation of the biomass 1*a*; 1*b*. The second gas injection applied by the second gas injectors 13 is controlled such that the environment of the second reactor section 7 above the biomass 1*a*; 1*b* is largely composed of pyrolysis product gas, where the air-fuel ratio is far below 1. The main pyrolysis of the biomass 1*a*; 1*b* in the second reactor section 7 is conducted at a temperature of about 600° C.

In the embodiment shown in FIG. 1A, the third reactor section 8 comprises third gas injectors 15 which are positioned below the transport unit 5 and which are arranged to output a third gas through the biomass 1*a*; 1*b* on the transport unit 5. The third reactor section 8 is primarily responsible for finishing the pyrolysis of the biomass 1*a*; 1*b* and further processing of the biomass 1*a*; 1*b* processed in second reactor zone 7. In other words, downstream further processing of the processed biomass 1*a*; 1*b* is achieved in a third reactor section 8 on the transport unit 5 downstream from the second reactor section 7 where this is labelled 'Zone 3' in the embodiment shown in FIG. 1A. The biomass 1*a*; 1*b* on the transport unit 5 enters the third reactor section 8 from the second reactor section 7. The biomass fuel on the moving bed 5 in the third reactor section 8 is still of high temperature, thus continuing release of any remaining volatile matter in the biomass 1*a*; 1*b* on the transport unit 5. The time spent by the biomass 1*a*; 1*b* on the transport unit 5 in the third reactor section 8 at high temperature can be controlled to prevent further pyrolysis of the biomass 1*a*; 1*b* that may otherwise lead to a lower yield.

The pyrolysis gas released from the biomass 1*a*; 1*b* on the transport unit 5 in the third reactor section 8 is transported away, partly by the third gas injection applied by the third gas injectors 15, towards the first and/or second reactor sections 6, 7.

Furthermore, the third gas is applied in a further embodiment for controlling composition of the processed biomass 1*b* at the output 3 of the reactor, the third gas may comprise steam in order to treat and cool the processed biomass 1*b*, or in more generic wording, the third gas is e.g. a cooling and/or product-optimizing gas. Alternatively or additionally, the third gas applied by the third gas injectors 15 may comprise carbon dioxide, in order to treat and cool the processed biomass 1*b*. The cooling of the processed biomass

1*b* cools it to a suitable temperature, before it enters the output 4 as the finished processed biomass product. A further option would be to provide a separate cooled wall 4*a* near the output 4, as shown in the cross sectional view of the FIG. 1A embodiment.

In a further specific embodiment, the third gas injectors 15 are arranged to supply steam. This allows to enhance the local hydrogen production. By removing the hydrogen gas locally a high quality $H_2$ output gas can be obtained. Furthermore, added radiation heat allows the temperatures of the char on the transport unit 5 to be high (e.g. >700° C.) which helps to enhance the reaction rate for $H_2$ production. It is estimated that the amount of $H_2$ in the gas in the reactor 1 can be as high as 40% using this embodiment, allowing to increase the caloric value of the produced gas. Use of steam at higher end temperature ranges can be used to activate the carbon in such a way that it will obtain a higher surface area and can be regarded a higher quality carbon product. The activation does not require a separate reactor but will take place at the end of the transport unit 5 where product optimization can be achieved by the final gas injection.

In the exemplary embodiment shown in FIG. 1A, the third reactor section 8 further comprises fourth gas injectors 16; 17 above the transport unit 5, arranged to output a fourth gas into the reactor during operation. In the exemplary embodiment, two different types of fourth gas injectors 16 and 17 are shown, which may each be provided with a different functionality. The fourth injectors indicated by reference numeral 16 may be operated in a similar manner to the first and second oxidant injectors 12, 14, i.e. inject a fourth gas into the reactor enclosure 2, e.g. aimed at increasing local gas-pressure to provide flow of gas throughout the reactor enclosure 2 from the third section 8 towards the first section 6 (and even into the outflow channel 21. Additionally or alternatively, the fourth gas injectors 17 may be provided which are arranged to inject a fourth gas in the form of an $O_2$ poor gas, e.g. recycle gas or $CO_2$ (for biochar or bio-coal optimization). It is noted that the fourth gas injectors 16; 17 allow to control the local temperature and thereby the amount of (local) radiation heat to the char on the transport unit 5. This makes it possible to optimize the char quality output by the reactor 1.

In summary, the first, second and third gas injectors 11, 13, 15 are further arranged to output a first, second, and third gas, respectively, each having a low oxygen content, and the first and second oxidant injectors 12, 14 are arranged to output an oxidizing gas only. The result is a reactor 1 allowing a process with controllable heat sources 12*a*, 14*a* from above the biomass 1*a*; 1*b* using volatiles escaping from the biomass 1*a*; 1*b* in the first and second reactor sections 6, 7, and subsequent post-processing of biomass 1*a*; 1*b*, i.e. drying, pyrolysis and/or gasification, cooling to obtain biochar or bio cokes (free from tar etc.).

In a further embodiment, the transport unit 5 comprises a transport grate, a moving grate, a transport auger, or a plurality of overlapping slides. In case of a transport grate, the transport unit 5 can be implemented as an endless belt type loop, with openings in the transport grate allowing the first, second and third gas to be injected into the biomass 1*a*; 1*b* on tip of the transport grating 5. In case of an implementation using overlapping slides, the openings for the first, second and third gas injectors 11, 13, 15 can be implemented as apertures in the respective vertical wall parts, e.g. in a staircase configuration of the overlapping slides. In the exemplary embodiment shown in FIG. 1A, the reactor 1 further comprises an outflow channel 21 in communication with the first, second and third reactor sections 6, 7, 8. This outflow channel 21 can be implemented as a closed off channel of the reactor 1, collecting the remaining volatiles and syngas products remaining from the pyrolysis process of the biomass 1*a*; 1*b* on the transport unit 5 and not used to fuel any one of the first or second heat sources 12*a*, 14*a*.

In the FIG. 1A embodiment, the reactor 1 further comprises a secondary oxidant injector 18 positioned in the outflow channel 21 near the first reactor section 6. The secondary oxidant injector 18 may be used to provide a secondary heat source 18*a* using locally remaining fuel like constituents to provide additional heat energy for the drying and pyrolysis process in the first reactor section 6.

In an even further embodiment, the reactor 1 further comprises a tertiary oxidant injector 19 positioned in the outflow channel 21 remote from the first, second and third reactor sections 6, 7, 8. The remote location 9 (indicated as Zone 4 in FIG. 1A) allows the remaining fuel constituents to be efficiently burnt using the tertiary oxidant injector 19 to provide a tertiary heat source 19*a* (e.g. with a temperature of as high as 1300° C.). This heat energy can be transported away from the reactor 1 for other applications or used locally to e.g. generate electrical energy. Alternatively, instead of the tertiary oxidant injector 19, the remaining flue gas from the pyrolysis process in reactor 1 can be used as a flue gas source, and/or (if the correct constituents are present) to produce syngas.

In a further exemplary embodiment, the reactor further comprises a control unit 20 connected to the first, second and third gas injectors 11, 13, 15 and the first and second oxidant injectors 12, 14, wherein the control unit 20 is arranged to control the amount and composition of gas mixture supplied by each of the first, second and third gas injectors 11, 13, 15 and the first and second oxidant injectors 12, 14. The control unit 20 is primarily responsible for controlling and correcting the local environment in the first, second and third reactor sections 6, 7, 8 to the optimal conditions for processing of biomass, e.g. for biochar production.

The reactor further comprises temperature sensors 22 positioned within the reactor enclosure 2 and connected to the control unit 20, wherein the control unit 20 is further arranged to control operational temperatures in the first, second, and third reactor section 6, 7, 8 separately, e.g. in order to optimize drying, pyrolysis and/or gasification of the biomass 1*a*; 1*b* in the various reactor sections 6, 7, 8. The temperature sensors 22 are e.g. arranged to measure temperature directly above the biomass 1*a*; 1*b* on the transport unit 5, e.g. by arranging the temperature sensors 22 through the heat-resistant material walls 2*a*.

In a further embodiment, the control unit 20 is arranged to control the operational temperatures in the first, second and/or third reactor section 6, 7, 8 to between 800° C. and 1400° C. in the gas phase. This allows an efficient biomass processing to be maintained within the reactor 1, e.g. by maintaining a temperature of between 600° C. and 650° C. directly above the biomass 1*a*; 1*b* in the second reactor section 7 for optimal pyrolysis. Note, however, that by adjusting all second gas injectors 13 and second oxidant injectors 14 this controlled temperature can be modified to operate between 400° C.-1000° C. directly above the biomass. During operation, the temperature of the transport unit 5 can optionally be measured using one or more sensors, and the control unit 20 may be further arranged to maintain the temperature of the transport unit 5 between 400° C. and 800° C., using the gas injectors 11, 13, 15 below the transport unit 5, e.g. in order to provide a longer lifetime of the transport unit 5.

The control unit 20 is connected to the moving bed 5 in an even further embodiment, and arranged to obtain a residence time of material on the moving bed 5 from the input 3 to the output 4 of between 10 to 120 minutes. The residence time is e.g. selected based on the amount and constituency of the biomass 1*a* entering the input 3 of the reactor 1, which can be manually input (e.g. based on data measured for batches of biomass material) or automatically based on associated sensor(s) near the input 3 of the reactor 1.

The temperature above the biomass 1*a*; 1*b* on the transport unit 5 is controlled in a further embodiment using gas injection below, respectively above the transport unit 5 in the first, second and third section 6, 7, 8. For example, the temperature sensors 22 may take a temperature measurement directly at the biomass 1*a*; 1*b* on the transport unit 5 in the first reactor section 6. The temperature sensors 22 may send a signal to the control unit 20, allowing temperature corrections for optimal biochar production. The control unit 20 may, for example, adjust the low oxygen content gas injection applied by the first oxidizing injectors 12 accordingly such that the optimal temperature conditions for biochar production in the first reactor section 6 are met.

FIG. 2 shows a schematic diagram of a control arrangement of a reactor for biochar production according to an embodiment of the present invention. The control arrangement for the reactor comprises a control unit 20, which is connected to the temperature sensors 22. The control unit 20 is further connected to the first, second and/or third gas injectors 11, 13, 15, the first and/or second oxidant injectors 12, 14, and, if present, fourth gas injectors 16, 17 and/or the secondary and/or tertiary injectors 18, 19. Also the control unit 20 is connected to the transport unit 5 to allow implementation of some of the embodiments described above.

It is noted that the elements described above to execute gas mixing in the reactor 1 also allow for the reactor 1 to be used as a conventional grate-combustion installation. Moreover, this gas mixing also allows for the changing of operation of the reactor 1 from combustion to gasification plus biochar production, which greatly enhances the flexibility in utilization of the described embodiments of the reactor 1

The present invention has been described above with reference to a number of exemplary embodiments as shown in the drawings. Modifications and alternative implementations of some parts or elements are possible, and are included in the scope of protection as defined in the appended claims.

The invention claimed is:

1. Reactor-A reactor for processing biomass, comprising a reactor enclosure having an input for receiving biomass and an output for outputting processed biomass;

a transport unit for transporting biomass in the reactor enclosure from the input to the output;

a first reactor section;

a second reactor section positioned downstream from the first reactor section;

a third reactor section positioned downstream from the second reactor section;

the first reactor section comprising first gas injectors which are positioned below the transport unit and which are arranged to output a first gas through the biomass on the transport unit during operation, and first oxidant injectors which are positioned above the transport unit and which are arranged to provide first heat sources generating and directing radiation heat energy to the biomass during operation;

the second reactor section comprising second gas injectors which are positioned below the transport unit and arranged to output a second gas through the biomass on the transport unit during operation, and second oxidant injectors which are positioned above the transport unit and which are arranged to provide second heat sources generating and directing radiation heat energy to the biomass during operation;

the third reactor section comprising third gas injectors which are positioned below the transport unit and arranged to output a third gas through the biomass on the transport unit during operation;

wherein the first, second and third gas injectors are further arranged to output a first, second, and third gas, respectively, each having a low oxygen content, and the first and second oxidant injectors are arranged to output an oxidizing gas only, further comprising a control unit connected to the first, second and third gas injectors and the first and second oxidant injectors, wherein the control unit is arranged to control the radiation heat energy from the first and second oxidant injectors in the first reactor section and the second reactor section, respectively, by controlling the amount and composition of gas mixture supplied by each of the first, second and third gas injectors and the first and second oxidant injectors.

2. The reactor according to claim 1, wherein the first and second oxidant injectors are positioned at a distance from the transport unit of at least 0.7 m.

3. The reactor according to claim 1, wherein the first gas is air, flue gas or a low oxygen content gas mixture, having a predefined composition with an equivalence ratio (ER) of less than 0.1.

4. The reactor according to claim 1, wherein the second gas is a gas with a low oxygen content.

5. The reactor according to claim 1, wherein the third gas is applied for controlling composition of the processed biomass at the output of the reactor.

6. The reactor according to claim 1, wherein the third gas injectors are arranged to supply steam.

7. The reactor according to claim 1, further comprising temperature sensors positioned within the reactor enclosure and connected to the control unit, wherein the control unit is further arranged to control operational temperatures in the first, second, and third reactor section separately.

8. The reactor according to claim 7, wherein the temperature sensors are arranged to measure temperature directly above the biomass on the transport unit.

9. The reactor according to claim 1, wherein the control unit is connected to the transport unit, and arranged to obtain a residence time of the biomass on the transport unit from the input to the output of between 10 to 120 minutes.

10. The reactor according to claim 1, wherein the third reactor section comprises fourth gas injectors above the transport unit, arranged to output a fourth gas into the reactor during operation.

11. The reactor according to claim 1, wherein the transport unit comprises a transport grate, a moving grate, a transport auger, or a plurality of overlapping slides.

12. The reactor according to claim 1, wherein the reactor further comprises an outflow channel in communication with the first, second and third reactor sections.

13. The reactor according to claim 12, wherein the reactor further comprises a secondary oxidant injector positioned in the outflow channel near the first reactor section.

14. The reactor according to claim 12, wherein the reactor further comprises a tertiary oxidant injector positioned in the outflow channel remote from the first, second and third reactor sections.

15. A method for processing biomass using a transport unit, comprising initial pyrolysis of the biomass in a first reactor section on the transport unit, forming pyrolysis gas by applying injection of a first gas through the biomass, and applying oxidant injection for reaction with the formed pyrolysis gas above the biomass on the transport unit, thereby providing radiation of heat energy onto the biomass in the first reactor section;

formation of processed biomass in a second reactor section on the transport unit downstream from the first reactor section, by pyrolysis of the biomass obtained by applying injection of a second gas through the biomass on the transport unit and combustion of the formed pyrolysis gas above the transport unit, thereby providing additional radiation of heat energy onto the biomass in the second reactor section;

downstream further processing of the processed biomass in a third reactor section on the transport unit downstream from the second reactor section, wherein the radiation heat energy in the first reactor section and the second reactor section, respectively, are controlled by actively controlling the amount and composition of gas mixture supplied as first gas and second gas, and the amount and composition of gas mixture supplied for oxidant injection, combustion and further processing.

16. The method according to claim 15, further comprising agitating the biomass on the transport unit, at least in the first and second reactor section.

17. The method according to claim 15, wherein the temperature above the biomass on the transport unit is controlled using gas injection both below and above the transport unit in the first, second and third section.

* * * * *